(12) United States Patent
Wu et al.

(10) Patent No.: US 7,737,302 B2
(45) Date of Patent: Jun. 15, 2010

(54) PROCESS FOR PREPARING BUPROPION HYDROCHLORIDE

(75) Inventors: Chaogang Wu, Dongyang (CN); Huayou Xiang, Dongyang (CN); Xianghua Yu, Dongyang (CN); Chun He, Dongyang (CN); Fengying Li, Dongyang (CN); Xianghong Shi, Dongyang (CN); Chengyue Lu, Dongyang (CN); Guoliang Chen, Dongyang (CN); Yangxiang Ge, Dongyang (CN)

(73) Assignee: Zhejiang Apeloa Medical Technology Co., Ltd., Zhejiang Province (CN)

( * ) Notice: Subject to any disclaimer, the term of this patent is extended or adjusted under 35 U.S.C. 154(b) by 0 days.

(21) Appl. No.: 12/216,513

(22) Filed: Jul. 7, 2008

(65) Prior Publication Data

US 2009/0012328 A1    Jan. 8, 2009

(30) Foreign Application Priority Data

Jul. 6, 2007    (CN)    ................. 2007 1 0069901

(51) Int. Cl.
*C07C 221/00*    (2006.01)
(52) U.S. Cl. ..................................... 564/343; 564/396
(58) Field of Classification Search ........................ None
See application file for complete search history.

(56) References Cited

U.S. PATENT DOCUMENTS 3,340,305 A * 9/1967 Jahn ............................ 568/316
3,819,706 A   6/1974 Mehta et al.
6,110,973 A * 8/2000 Young ......................... 514/649

FOREIGN PATENT DOCUMENTS

WO    WO 2004/024674    3/2004

OTHER PUBLICATIONS

XU1 CASREACT 148:217184, 2006. Abstract of (Studies on the synthesis of bupropion hydrochloride; Anhui Daxue Xuebao, Ziran Kexueban (2006), 30(5), 87-90.).*
XU2 CASREACT 148:217184, 2006. Abstract of (Studies on the synthesis of bupropion hydrochloride; Anhui Daxue Xuebao, Ziran Kexueban (2006), 30(5), 87-90.).*
Dandala et al., Derwent abstract of IN 200401323 I4, published Jun. 22, 2007.*
Ke et al. "Studies on the Synthesis of Bupropion hydrocholorid." Chinese Journal of Medicinal Chemistry, vol. 13, No. 5, Oct. 2003, pp. 286-287 (Translation and Abstract).
Musso et al. "Synthesis and Evaluation of the Anticonvulsant Activity of a Series of 2-Amino-1-Phenyl-1-Propanols Derived From the Metalbolites of the Antidepressant Bupropion." Bioorganic & Medicinal Chemistry Letters, vol. 7, No. 1, 1997. pp. 1-6.
Min et al. "Study on Synthesis of the Amfebutamone Hydrochloride." Shandong Chemical Industry, vol. 32, No. 3, 2003. pp. 31-33. (Translation and Abstract).
Ziao et al. "Studies on the Synthesis of Bupropion Hydrochloride." Journal of Anhui University, vol. 30, No. 5, Sep. 2006, pp. 87-90. (Translation and Abstract).

* cited by examiner

*Primary Examiner*—Rosalynd Keys
(74) *Attorney, Agent, or Firm*—Jacobson Holman PLLC

(57) ABSTRACT

This invention described a synthesis method of bupropion hydrochloride. m-chloropropiophenone was brominated directly with bromine, then aminated with t-butylamine and finally reacted with HCl to obtain crude product of bupropion hydrochloride. Pure product was obtained after recrystallization. This method is convenient and suitable for commercial manufacturing because of low cost of production, high yield, less byproducts and being environmental friendly.

7 Claims, No Drawings

PROCESS FOR PREPARING BUPROPION HYDROCHLORIDE

FIELD OF THE INVENTION

This invention is about a process for preparing a medicine for depression, more particularly, a process for preparing bupropion hydrochloride.

BACKGROUND OF THE INVENTION

Bupropion hydrochloride, whose chemical name is (±)-1-(3-chlorophenyl)-2-[(1,1-dimethylethyl)aminol]-1-propanone hydrochloride, is a medicine for depression developed by Glaxo Wellcome. Processes for preparing Bupropion hydrochloride have been reported in the literature, such as Chen Ke, et al. described in Chinese Journal of Medicinal Chemistry, Vol. 13, No. 5, 2003 that bupropion hydrochloride can be prepared from 3-chloropropiophenone by chlorination with cupric chloride, amination with t-butylamine, acidification with hydrogen chloride-isopropanol. Even though this method is highly selective and easy to operate, it is costly to treat the waste residue produced by chlorination, which causes environmental problems. This restrains industrial production.

A method reported by Xia Min, et al. for preparation of Bupropion hydrochloride used m-chlorobenzoyl chloride as starting material, after bromination and N-alkylation, bupropion hydrochloride was obtained. N-Bromo succinimide was used for bromination to avoid direct bromination with bromine. The yield of bromination was increased. Polyethylene glycol (PEG) was used as phase-transfer catalyst (PTC) in the N-alkylation reaction to achieve high yield. But this method is not suitable for mass production because of the high cost of the bromination reagent.

As Xu Ziao, et al. described in the *Journal of Anhui University*, m-chlorobenzoyl chloride was used for raw material. After acylation, Grignard reaction, bromination, and N-alkylation, bupropion hydrochloride was obtained. Although this method is convenient and the total yield is high, the raw material hydrolyzes easily and its quality is not stable, which affects yield and quality of finish product. Therefore, commercial production becomes impractical.

The U.S. Pat. No. 3,819,706 introduced a method for preparation of using m-chlorobenzonitrile as raw material. After Grignard reaction, bromination and amination with t-butylamine, the objective product was obtained. Grignard Reaction requires anhydrous operation, and bromination is hard to control and results in excessive byproducts which are hard to removed in post processing and decrease yield.

The Patent WO2004024674 described that bupropion free base was obtained from m-chloropropiophenone via bromination in the presence of t-butylamine, and then reacted with hydrochloric acid to obtain bupropion hydrochloride. Because t-butylamine is a solvent as well as a reactant in bromination step, this method increases side reactions and cost of production therefore restrains commercial manufacture.

As David L. Musso described (Bioorganic & Medicinal Chemistry Letter, Vol. 7, No. 1. pp. 1-6, 1997), m-chlorobenzoic acid was used as starting material, in the presence of thionyl chloride, ammonium hydroxide and 1,4-dioxane to produce m-chlorobenzonitrile Benzonitrile, then Grignard reaction, bromination and substitution, the target product of bupropion was obtained. This preparation had a long process, complicated operations, high pressure on environment and low yield, also had strict requirements for operations. Therefore, it is not suitable for large scale production.

The methods of prior art for producing bupropion hydrochloride generally have high cost of production, low yields, high requirements for safety, high pressure on environment and long cycle of production.

SUMMARY OF THE INVENTION

The present invention provides an efficient, low-cost synthesis method of bupropion hydrochloride for commercial manufacturing.

A method for synthesizing bupropion hydrochloride wherein the compound of formula (I) is prepared from m-chloropropiophenone via bromination with bromine to obtain the compound of formula (II), amination with t-butylamine to obtain the compound of formula (III), reacting with HCl to obtain the compound of formula (I) (bupropion hydrochloride).

Structural formulae for the said compound I~III and the chemical reactions are shown in the following scheme:

bromination

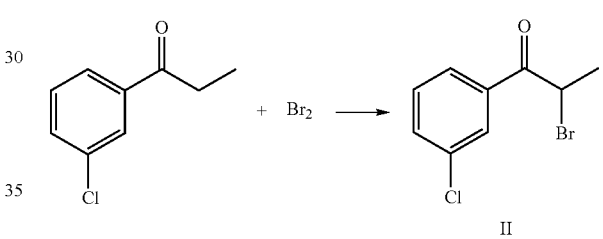

amination

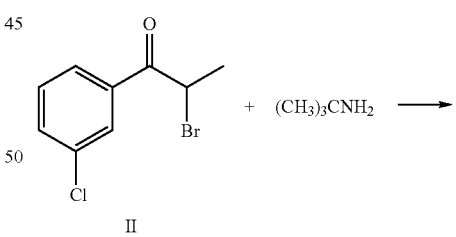

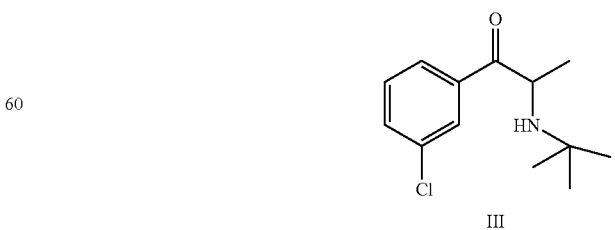

Formation of bupropion hydrochloride

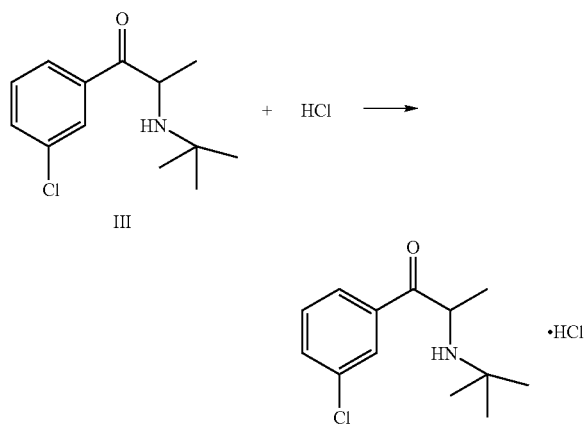

The said synthesis of bupropion hydrochloride comprising the steps of

A) Bromination

Bromine was added dropwise to m-chloropropiophenone and the reaction was kept for 2 to 6 hours at the temperature in the range of 50 to 100° C. to obtain the compound of formula (II)(m-chloro-α-bromopropiophenone);

B) Amination t-Butylamine was added to the reaction mixture of step A and the mixture was stirred for 2 to 6 hours under refluxing. After removal of the excessive t-butylamine, the concentrated solution was then extracted to obtain an organic phase which was washed with water and dried with desiccant to obtain an organic solution containing compound of formula (III)

C) Formation of Bupropion Hydrochloride

The organic solution of compound of formula III reacted with HCl and formed bupropion hydrochloride, the crude product was filtered out. The total yield was 70%-80%.

The molar ratio of starting material of the said synthesis is:
m-chloropropiophenone 1
Bromine 0.9-1.1
t-Butylamine 4-10
Hydrochloride 0.8-1.5

In step A, m-chloropropiophenone can react with bromine directly or in the presence of other solvent. That is, adding bromine dropwise to the mixture of m-chloropropiophenone and a solvent. The said solvent can be an alkyl halide. The said alkyl halide was selected from dichlomethane, chloroform, carbon tetrachloride or dichloroethane. In step A, 5-15 ml of solvent for every 1 gram of m-chloropropiophenone was used if solvent was used in the bromination reaction. The solvent was removed by evaporation under reduced pressure at temperature below 70° C. after bromination or removed by distillation along with the excessive t-butylamine in step B.

If solvent was not added to the reaction mixture of step A or had been removed by evaporation under reduced pressure after bromination reaction, still a solvent could be added to the reaction mixture of step B. Thus, a solvent could be added to the reaction system obtained from step A prior to addition of t-butylamine. The said solvent added in step B could be an alkyl halide or a mixture of acetone and water. The said alkyl halide was selected from dichloromethane, chloroform, carbon tetrachloride or dichloroethane. The said mixture of acetone and water had a mass ratio in the range of 2-10:1. The solvent in step B was removed by evaporation along with the excessive t-butylamine.

In the said synthesis of bupropion hydrochloride, compound of formula (II) from step A was used in the next reaction without purification.

In the said synthesis of bupropion hydrochloride, the temperature was kept below 150° C. in the concentration process after amination reaction in step B.

In the said synthesis of bupropion hydrochloride, the mass ratio of m-chloropropiophenone: extracting mixture used after amination reaction of step B was 1:5-15. The mass ratio of organic solvent : water in the extracting mixture was 5:1-5. Water was used to remove hydrobromic acid salt of t-butylamine which could be reused after neutralization treatment. The organic solvent in the extraction mixture was selected from toluene, methyl formate, methyl acetate, ethyl formate, ethyl acetate, butyl acetate, ethyl butyrate, xylene, dichloromethane, chloroform, carbon tetrachloride dichloroethane.

In the said desiccant was selected from anhydrous magnesium sulfate or anhydrous sodium sulfate.

In the said synthesis of bupropion hydrochloride, the organic solution of compound of formula (III) was evaporated to dryness and then reacted with a solution HCl gas in an organic solvent. The solvent to dissolve HCl gas was selected from methanol, ethanol, propanol, isopropanol, butanol, 2-butanol, isobutanol, t-butanol, toluene, methyl formate, methyl acetate, ethyl formate, ethyl acetate, butyl acetate, ethyl butyrate, xylene, dichloromethane, chloroform, carbon tetrachloride or, dichloroethane.

The organic solution of compound of formula (III) could react with HCl gas or a solution of HCl gas in an identical organic solvent directly without concentration in step C.

When the said organic solvent to dissolve HCl gas is identical to the organic solvent used for extraction in step B, it is more convenient to recycle and treat the solvent. Quantity of the organic solvent to dissolve HCl gas was determined by the molar ratio of m-chloropropiophenone to HCl. Saturated HCl solution was used to reduce the quantity of organic solvent as much as possible. When HCl gas was used directly, the PH value of the reaction mixture should be 4 or lower at the end of reaction.

When the organic solution of compound of formula (III) was concentrated to dryness and then reacted with an organic solution of HCl gas in step C, it was not necessary to use an identical solvent to dissolve HCl gas to the solvent used for extraction in step B.

The said crude product of bupropion hydrochloride obtained from step C needs to be refined in order to obtain product of higher purify.

The crude product of bupropion hydrochloride was dissolved in ester, alcohol or the mixture of alcohol and water, and then decolorized with activated carbon and filtered to remove activated carbon. The filtrate was cooled and bupropion hydrochloride crystallized. After filtered and dried in vacuum (−0.04~−0.09 MPa) at the temperature in the range of 40-100° C. for 3 to 8 hours, pure product of bupropion hydrochloride was obtained.

The quantity of solvent used for refining was 3~15 time better than that of the crude bupropion hydrochloride, preferably 5~10 times. The said ester used as solvent could be methyl formate, ethyl formate, methyl acetate, ethyl acetate, butyl acetate, ethyl butyrate; the said alcohol could be methanol, ethanol, propanol, isopropanol, butanol, 2-butanol, isobutanol, t-butanol, the said mixture of water and alcohol was in the range of 1:3~20 volume ratio.

This invention is suitable for commercial manufacturing because of the low-cost, high quality of the product, low-pollution.

DETAILED DESCRIPTION OF THE INVENTION

EXAMPLES

Example 1

The reactions were carried out according to a molar ratio of m-chloroprophenone:bromine:t-butylamine:HCl in 1:0.92:5:1.

To 1 mole of m-chloroprophenone heated to 75±5° C., bromine was added dropwise under stirring, and the reaction temperature was kept at 75±5° C. during the addition and kept for 3 hours after the addition, m-chloro-α-bromopropiophenone (compound of formula (II)) was obtained. t-Butylamine was added to m-chloro-α-bromopropiophenone obtained above and the reaction mixture was refluxed for 5.5 hours. After excessive t-butylamine was evaporated below 100° C., the concentrated solution was cooled down to room temperature and then extracted with 1000 ml of toluene and 200 ml of water. The organic phase was dried with anhydrous magnesium sulfate (20 g) to obtain a solution of bupropion free base (compound III). HCl gas was bubbled into the solution of bupropion free base at room temperature until the PH value the reaction mixture was less than or equal to 4. After filtration, crude product of bupropion hydrochloride was obtained. The crude product of bupropion hydrochloride was dissolved in 1500 ml of ethyl acetate heated to 60° C., and decolorized with activated carbon (3 g) for 30 minutes and filtered. Then filtrate was cooled down, crystal bupropion hydrochloride crystallized. Wet product of bupropion hydrochloride was obtained after filtration and was dried in vacuum (−0.04~−0.09 MPa, 60±5° C.) for 5 hours to obtain pure product. Total yields was 75% based on m-chloropropiophenone; HPLC's purify was over 99.9%.

Example 2

The reaction were carried out according to a mole ratio of m-chloropropiophenon:bromine:t-butylamine:HCl in 1:0.97:8:1.2.

To 1 mole of m-chloropropiophenone heated to 60±5° C., bromine was added dropwise under stirring. The reaction temperature was kept at 60±5° C. during the addition of bromine, and kept for 5.5 hours after the addition. m-Chloro-α-bromopropiophenone (compound of formula (II)) was obtained.

t-Butylamine was added to m-chloro-α-bromopropiophenone obtained above and the reaction mixture was refluxed for 3 hours. Excessive t-butylamine was removed by evaporation below 80° C. The concentrated solution was cooled down to room temperature and then extracted with 800 ml of ethyl acetate and 280 ml of water. The organic phase was dried with anhydrous magnesium sulfate (15 g) to obtain a solution of bupropion free base. A solution of HCl in ethyl acetate was added at room temperature to the organic phase. Crude product of bupropion hydrochloride was obtained after filtration. The crude product of bupropion hydrochloride was dissolved in 1200 ml of methanol and 120 ml of water at 80° C., decolorized with activated carbon (5 g) for 20 minutes and filtered. The filtrate was cooled and filtered to obtain wet product of bupropion hydrochloride. The wet product was dried in vacuum (−0.04~−0.09 MPa, 80° C.) for 3 hours to obtain pure product. Total yield was 70% based on m-chloropropiophenone, and the HPLC's purify was higher than or equal to 99.9%.

Example 3

The reactions were carried out according to a mole ratio of m-chloropropiophenone:bromine:t-butylamine:HCl in: 1:1.05:6:0.8.

To 1 mole of m-chloropropiophenone was heated to 70±5° C., bromine was added dropwise under stirring. The reaction temperature was kept at 70±5° C. during the addition of bromine and kept for 5.5 hours after the addition. m-chloro-α-bromopropiophenone (compound of formula (II)) was obtained.

t-Butylamine was added to a solution of m-chloro-α-bromopropiophenone obtained above in acetone and water and the reaction mixture was refluxed for 2.5 hours. Acetone, water and excessive t-butylamine was evaproated at the temperature of 120° C. The concentrated solution was cooled down to room temperature and then extracted with 1500 ml of chloroform and 250 ml of water. The organic phase was dried with anhydrous sodium sulfate (30 g) and concentrated to dryness under reduced pressure. A solution of HCl in ethanol was added to the concentrated solution at room temperature and a crude product of bupropion hydrochloride was obtained after filtration. The crude product of bupropion hydrochloride was added to 2000 ml ethanol and heated to 70° C., decolorized by activated carbon (2 g) for 30 minutes and filtered. The filtrate was cooled and filtered to obtain wet product of bupropion hydrochloride. The wet product was dried in vacuum (−0.04~−0.09 MPa, 70° C.) for 4 hours to obtain pure product. Total yield was 72% based on m-chloropropiophenone; and the HPLC's purify was ≧99.9%.

Example 4

The reactions were carried out in accordance with a mole ratio of m-chloropropiophenone:bromine:t-butylamine:HCl in 1:1:10:1.5.

A mixture of 1 mole of m-chloropropiophenone and dichoroethane was heated to 65±5° C. Bromine was added dropwise to this mixture under stirring. The reaction temperature was kept at 65±5° C. during the addition of bromine and kept for 5 hours after the addition. Dichloroethane was then evaporated under reduce pressure at 60° C. m-Chloro-α-bromopropiophenone (compound of formula (II)) was obtained.

After t-Butylamine was added to the compound obtained above, the reaction mixture was refluxed for 2.5 hours. Excessive t-butylamine was evaporated at 140° C. The concentrated solution was cooled down to room temperature and then extracted with a mixture of 1200 ml of ethyl formate and 260 ml of water. The organic phase was dried with 25 g anhydrous sodium sulfate to obtain a solution of bupropion free base. Then a solution of HCl in ethyl formate was added at room temperature. Crude product of bupropion hydrochloride was obtained after filtration. The crude product was added to a mixture of dissolved in 1400 ml of isopropanol and 700 ml of water heated to 90 ° C., decolorized with activated carbon (8 g) for 40 minutes and filtered. The filtrate was cooled down and filtered to obtain wet product of bupropion hydrochloride. The wet product was dried in vacuum (−0.04~−0.09

MPa, 90° C.) for 2 hours to obtain pure product. Total yield was 80% based by m-chloropropiophenoone; and the HPLC's purify was ≧99.9%.

Example 5

The reactions were carried out in accordance with a mole ratio of m-chloropropiophenone:bromine:t-butylamine:HCl in 1:1.08:4:1.3.

To 1 mole of m-chloropropiophenone heated to 85±5° C., bromine was added dropwise under stirring. The reaction temperature was kept at 85±5° C. during and after the addition of bromine, and the reaction was carried on for 2 hours. Then m-chloro-α-bromopropiophenone (compound of formula (II)) was obtained.

t-Butylamine was added to the compound above and the reaction mixture was refluxed for 5 hours. Excessive t-butylamine was evaproated at 90° C. The concentrated solution was cooled down to room temperature and then extracted with a mixture of 1400 ml of dichloromethane and 220 ml of water. The organic phase was dried with 20 g anhydrous magnesium sulfate to obtain a solution of bupropion free base. The solution of HCl in dichloromethane was added at room temperature. Crude product of bupropion hydrochloride was obtained after filtration. The crude product was dissolved in a mixture of 1800 ml of ethanol and 100 ml of water that was heated to 75° C., then decolorized with activated carbon (7 g) for 30 minutes and filtered. The filtrate was cooled down and filtered to obtain wet product of bupropion hydrochloride. The wet product was dried in vacuum (−0.04~−0.09 MPa, 50° C.) for 7 hours to obtain pure product. Total yield was 78% based on m-chloropropiophenone; and the HPLC's purify was ≧99.9%.

The invention claimed is:

1. A process for preparing bupropion hydrochloride (I), comprising the steps of:
    (A) obtaining m-chloropropiophenone, bromine, t-butylamine and hydrochloride in the molar ratio of: 1:0.9-1.1:4-10:0.8-1.5;
    (B) brominating m-chloropropiophenone directly with bromine without addition of a solvent to obtain compound (II), wherein m-chloropropiophenone is firstly heated to a temperature in the range of 50 to 100° C., then bromine is added dropwise to m-chloropropiophenone and reacted with m-chloropropiophenone for 2 to 6 hours at the temperature in the range of 50 to 100° C. to form compound II (m-chloro-α-bromopropiophenone);
    (C) without purification of the product of said brominating step, aminating compound (II) with t-butylamine to obtain compound (III), wherein t-Butylamine is added to the reaction mixture of bromination and stirred under refluxing for 2 to 6 hours, after removal of redundant t-butylamine, concentrated solution obtained is then extracted by a solution with an organic solvent and water in 5:1-5 mass ratio, organic phase is washed with water and dried with a drying agent to obtain an organic solution of compound III, and
    (D) reacting compound (III) with hydrogen chloride gas directly to form salt and obtain bupropion hydrochloride (I), which is precipitated and filtered to obtain compound I;
    (E) crude product of bupropion hydrochloride obtained in step (D) is dissolved in a solvent of ester, alcohol, or mixture of alcohol and water and decolorized with activated carbon which is removed by filtration, the filtrate is cooled to crystallize bupropion hydrochloride which was filtered and dried in vacuum; the drying temperature in vacuum is in the range of 40 to 100° C.; the time for drying may vary from 3 to 8 hours; the vacuum is in the range of −0.04 to −0.09 MPa, wherein the amount of the ester, alcohol or mixture of alcohol and water is 3 to 15 times of the weight of the crude product of bupropion hydrochloride; the said ester is methyl formate, ethyl formate, methyl acetate, ethyl acetate, butyl acetate, ethyl butyrate, said alcohol is methanol, ethanol, propanol, isopropanol, butanol, sec-butanol, isobutanol or tert-butanol;

wherein the structure of the compounds I, II and III are:

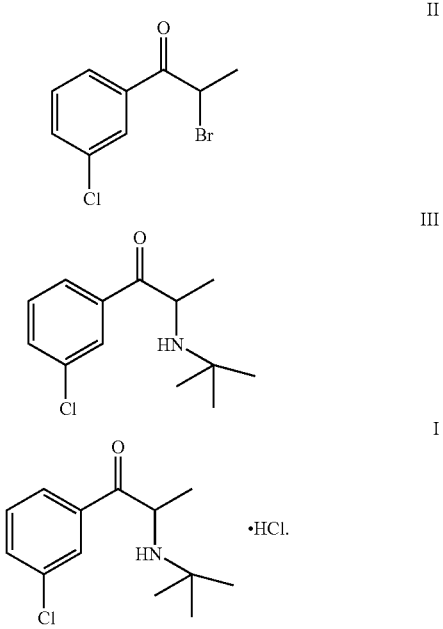

2. The process according to claim 1, wherein the organic solvent for extraction in step (C) is *toluene*, methyl *formate*, methyl *acetate*, ethyl *formate*, ethyl *acetate*, butyl *acetate*, ethyl *butyrate*, *xylene*, dichloromethane carbon tetrachloride or *dichloroethane*; said drying agent is anhydrous magnesium sulfate or sodium *sulfate*.

3. The process according to claim 2, wherein the mixture of water and alcohol is in 1:3-20 volume ratio.

4. A process for preparing bupropion hydrochloride (I), comprising the steps of:
    (A) obtaining m-chloropropiophenone, bromine, t-butylamine and hydrochloride in the molar ratio of: 1:0.9-1.1:4-10:0.8-1.5;
    (B) brominating m-chloropropiophenone directly with bromine without addition of a solvent to obtain compound (II), wherein m-chloropropiophenone is firstly heated to a temperature in the range of 50 to 100° C., then bromine is added dropwise to m-chloropropiophenone and reacted with m-chloropropiophenone for 2 to 6 hours at the temperature in the range of 50 to 100° C. to form compound (II) (m-chloro-α-bromopropiophenone);
    (C) without purification of the product of said brominating step, aminating compound (II) with t-butylamine to obtain compound (III), wherein t-butylamine is added to the reaction mixture of bromination and stirred under refluxing for 2 to 6 hours, after removal of redundant t-butylamine, concentrated solution obtained is then extracted by a solution with an organic solvent and water in 5:1-5 mass ratio, organic phase is washed with water and dried with a drying agent to obtain an organic solution of compound (III), and (D) reacting the organic solution of compound (III) with an organic solution of hydrogen chloride gas to form salt and obtain bupropion hydrochloride (I), which is precipitated and filtered to obtain compound (I);

(E) crude product of bupropion hydrochloride obtained in step (D) is dissolved in a solvent of ester, alcohol, or mixture of alcohol and water and decolorized with activated carbon which is removed by filtration, the filtrate is cooled to crystallize bupropion hydrochloride which was filtered and dried in vacuum; the drying temperature in vacuum is in the range of 40 to 100° C.; the time for drying may vary from 3 to 8 hours; the vacuum is in the range of −0.04 to −0.09 MPa, wherein the amount of the said ester, alcohol or mixture of alcohol and water is 3 to 15 times of the weight of the crude product of bupropion hydrochloride; the ester is methyl formate, ethyl formate, methyl acetate, ethyl acetate, butyl acetate, ethyl butyrate, said alcohol is methanol, ethanol, propanol, isopropanol, butanol, sec-butanol, isobutanol or tert-butanol;

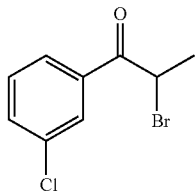

II

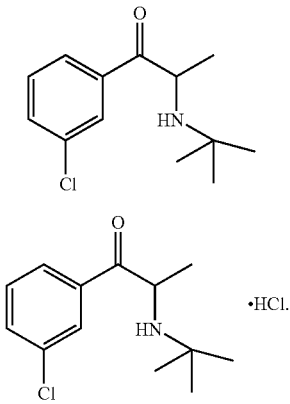

III

I

5. The process according to claim 4, wherein the organic solvent for extraction in step (C) is toluene, methyl formate, methyl acetate, ethyl formate, ethyl acetate, butyl acetate, ethyl butyrate, xylene, dichloromethane carbon tetrachloride or dichloroethane; said drying agent is anhydrous magnesium sulfate or sodium sulfate.

6. The process according to claim 5, wherein the solvent of hydrogen chloride gas is selected from the group consisting of methanol, ethanol, propanol, butanol, sec-butanol, isobutanol, tert-butanol, toluene, methyl formate, methyl acetate, ethyl formate, ethyl acetate, butyl acetate, ethyl butyrate, xylene, dichloromethane, chloroform, carbon tetrachloride and dichloroethane.

7. The process according to claim 6, wherein the mixture of water and alcohol is in 1:3-20 volume ratio.

* * * * *